(12) United States Patent
Venturino et al.

(10) Patent No.: US 8,519,213 B2
(45) Date of Patent: *Aug. 27, 2013

(54) STABILIZED ABSORBENT COMPOSITE (75) Inventors: Michael Barth Venturino, Appleton, WI (US); Daniel Robert Schlinz, Greenville, WI (US); John Timothy Hahn, Merrill, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/467,722

(22) Filed: May 9, 2012

(65) Prior Publication Data

US 2012/0271262 A1     Oct. 25, 2012

Related U.S. Application Data (63) Continuation of application No. 11/408,301, filed on Apr. 21, 2006, now Pat. No. 8,198,506.

(51) Int. Cl.
*A61F 13/15* (2006.01)
(52) U.S. Cl.
USPC .............................. 604/378; 604/380; 604/383
(58) Field of Classification Search
USPC .......................................... 604/378–380, 383
See application file for complete search history.

(56) References Cited

U.S. PATENT DOCUMENTS

| | | |
|---|---|---|
| 3,620,894 A | 11/1971 | Oates |
| 3,812,001 A | 5/1974 | Ryan |
| 3,889,679 A | 6/1975 | Taylor |
| 3,927,673 A | 12/1975 | Taylor |
| 4,704,116 A | 11/1987 | Enloe |
| 4,798,603 A | 1/1989 | Meyer et al. |
| 4,892,535 A | 1/1990 | Bjornberg et al. |
| 5,114,781 A | 5/1992 | Morman |
| 5,116,662 A | 5/1992 | Morman |
| 5,176,668 A | 1/1993 | Bernardin |
| 5,192,606 A | 3/1993 | Proxmire et al. |
| 5,458,592 A | 10/1995 | Abuto et al. |
| 5,486,166 A | 1/1996 | Bishop et al. |
| 5,490,846 A | 2/1996 | Ellis et al. |
| 5,496,298 A | 3/1996 | Kuepper et al. |
| 5,509,915 A | 4/1996 | Hanson et al. |
| 5,609,588 A | 3/1997 | DiPalma et al. |
| 5,645,542 A | 7/1997 | Anjur et al. |
| 5,785,697 A | 7/1998 | Trombetta et al. |
| 5,873,963 A | 2/1999 | Trombetta et al. |
| 5,883,028 A | 3/1999 | Morman et al. |

(Continued)

FOREIGN PATENT DOCUMENTS

| | | |
|---|---|---|
| EP | 0 758 543 A1 | 2/1997 |
| WO | WO 03/051254 A2 | 6/2003 |

*Primary Examiner* — Lynne Anderson
(74) *Attorney, Agent, or Firm* — Sarah Ann Dressel (57) ABSTRACT An absorbent article includes a liquid pervious liner, a liquid impervious back sheet, and an absorbent composite located between the liner and the back sheet. The absorbent composite includes a first sheet, a second sheet, and a unitary absorbent core. The unitary absorbent core has a plurality of holes there through, wherein each hole has an area less than 200 mm². The unitary absorbent core has a uniform density and is positioned between the first sheet and the second sheet. The first sheet is directly joined with the second sheet at a plurality of bond points. The bond points are located within the holes and are substantially devoid of absorbent material.

25 Claims, 7 Drawing Sheets

(56) References Cited

U.S. PATENT DOCUMENTS

| | | |
|---|---|---|
| 5,925,026 A | 7/1999 | Arteman et al. |
| 5,961,757 A | 10/1999 | Trombetta et al. |
| 5,964,743 A | 10/1999 | Abuto et al. |
| 6,152,906 A | 11/2000 | Faulks et al. |
| 6,220,999 B1 | 4/2001 | Kugler et al. |
| 6,231,557 B1 | 5/2001 | Krautkramer et al. |
| 6,238,379 B1 | 5/2001 | Keuhn et al. |
| 6,287,403 B1 | 9/2001 | Couillard et al. |
| 6,362,389 B1 | 3/2002 | McDowall et al. |
| 6,454,690 B2 | 9/2002 | Kugler et al. |
| 6,552,245 B1 | 4/2003 | Roessler et al. |
| 6,627,130 B2 | 9/2003 | Kugler et al. |
| 6,630,096 B2 | 10/2003 | Venturino et al. |
| 6,830,800 B2 | 12/2004 | Curro et al. |
| 6,884,494 B1 | 4/2005 | Curro et al. |
| 7,718,021 B2 | 5/2010 | Venturino et al. |
| 8,198,506 B2 * | 6/2012 | Venturino et al. ............ 604/378 |
| 2002/0102392 A1 | 8/2002 | Fish et al. |
| 2003/0045851 A1 | 3/2003 | Vartiainen |
| 2003/0139721 A1 | 7/2003 | Melius et al. |
| 2004/0098838 A1 | 5/2004 | Venturino et al. |
| 2004/0162536 A1 | 8/2004 | Becker et al. |
| 2005/0256495 A1 | 11/2005 | Schlinz et al. |
| 2006/0004334 A1 | 1/2006 | Schlinz et al. |
| 2006/0065354 A1 | 3/2006 | Mischler et al. |
| 2006/0135932 A1 | 6/2006 | Abuto et al. |
| 2007/0044903 A1 | 3/2007 | Wisneski et al. |
| 2007/0246147 A1 | 10/2007 | Venturino et al. |
| 2007/0250026 A1 | 10/2007 | Venturino et al. |

* cited by examiner

STABILIZED ABSORBENT COMPOSITE

This application is a continuation of application Ser. No. 11/408,301 filed on Apr. 21, 2006 now U.S. Pat. No. 8,198,506. The entirety of application Ser. No. 11/408,301 is hereby incorporated by reference.

BACKGROUND OF THE INVENTION

The present invention relates to stabilized absorbent composites and methods for making stabilized absorbent composites. The absorbent composites of the present invention are suitable for incorporation into a variety of disposable absorbent articles such as, for example, diapers, children's training pants, adult incontinence pads and garments, menstrual pads, bed pads, surgical drapes, and the like.

Conventional absorbent composites have traditionally been made of cellulosic fluff or other fibrous materials. Many have also included superabsorbent particles dispersed within the fibrous materials. However, many of these traditional absorbent composites have suffered from structural breakdowns during use, including, for example, cracking, separating, wadding, and/or "roping." These problems are generally undesirable and may cause discomfort for the wearer and/or may limit the performance of the absorbent composite.

Additionally, some conventional absorbent composites have exhibited undesirable "gel-on-skin" wherein some of the superabsorbent particles escape the absorbent composite and stick to the wearer during use. This problem may be worse with absorbent articles having a higher amount of superabsorbent material as a percentage of the total absorbent material weight.

Various attempts to prevent or minimize structural breakdowns and superabsorbent losses have included, for example, densifying the cellulosic fluff, adding adhesives or other binding agents to the absorbent material, wrapping the absorbent material in nonwovens or tissues, point bonding the absorbent core, aperturing the absorbent core, needling the absorbent core, placing the superabsorbent material in pockets or discrete layers, among others. However, there still exists a need for stabilized absorbent composites that minimize or eliminate structural breakdowns and superabsorbent losses.

SUMMARY OF THE INVENTION

In response to the discussed need, the present invention provides an absorbent article that includes a liquid pervious liner, a liquid impervious back sheet, and an absorbent composite located between the liner and the back sheet. The absorbent composite includes a first sheet, a second sheet, and a unitary absorbent core. The unitary absorbent core has a plurality of holes there through and each hole has a hole area less than 200 mm². The unitary absorbent core has a uniform density and is positioned between the first sheet and the second sheet. The first sheet is directly joined with the second sheet at a plurality of bond points. The bond points are located within the holes and are substantially devoid of absorbent material.

In various embodiments, the first sheet and the second sheet may be made of tissue and may be joined together at the bond points by adhesive.

In various embodiments, the first sheet and the second sheet may be made of nonwoven material and may be joined together at the bond points by adhesive.

In various embodiments, the unitary absorbent core may include 50 to 90 percent superabsorbent particles and 50 to 10 percent cellulose fluff fibers by weight.

In various embodiments, the absorbent composite may have a thickness of less than 6 mm.

In various embodiments, at least 90 percent of the holes have a bond point registered therein.

In various embodiments, the holes may have a circular shape and each hole may have an area of 1 mm² to 25 mm².

In various embodiments, the absorbent core defines a total absorbent core area and the hole areas define a total hole area that may be less than 25 percent of the total absorbent core area.

In various embodiments, each bond point defines a bond area that may be at least 60 percent or at least 70 percent of the hole area.

In various embodiments, the bond points may have a diameter and may be separated by at least four times the diameter.

In various embodiments, the unitary absorbent core defines a perimeter and the absorbent composite may include a flange extending about the entire perimeter.

In various embodiments, the bond points may be skewed towards the second sheet.

In another embodiment, the present invention provides an absorbent article that includes a liquid pervious liner, a liquid impervious back sheet, and an absorbent composite located between the liner and the back sheet. The absorbent composite includes a first sheet, a second sheet, and a unitary absorbent core. The unitary absorbent core has a plurality of holes there through and each hole has a hole area less than 200 mm². The unitary absorbent core has a uniform density and is positioned between the first sheet and the second sheet. The first sheet is directly joined with the second sheet at a plurality of bond points, the bond points are registered within the holes, and the bond points are substantially devoid of absorbent material.

In various embodiments, the first sheet and the second sheet may be made of nonwoven material and may be joined together at the bond points by adhesive.

In various embodiments, the unitary absorbent core may include 50 to 90 percent superabsorbent particles and 50 to 10 percent cellulose fluff fibers by weight.

In various embodiments, the absorbent composite may have a thickness of less than 6 mm, the holes may have a circular shape, each hole may have an area of 1 mm² to 25 mm², and each bond point defines a bond area and the bond area may be at least 80 percent of the hole area.

In various embodiments, the bond points may be skewed towards the second sheet.

In another embodiment, the present invention provides an absorbent article that includes a liquid pervious liner, a liquid impervious back sheet, and an absorbent composite located between the liner and the back sheet. The absorbent composite includes a first sheet made of nonwoven material, a second sheet made of nonwoven material, and a unitary absorbent core having a plurality of holes there through. The unitary absorbent core has 50 to 90 percent superabsorbent particles and 50 to 10 percent cellulose fluff fibers by weight, the unitary absorbent core has a uniform density and is positioned between the first sheet and the second sheet. The first sheet extends through the holes and is directly joined with the second sheet at a plurality of bond points by adhesive. The bond points are skewed towards the second sheet and are registered within the holes. The holes have hole areas and the bond points having bond areas wherein the bond areas are at least 70 percent of the hole areas.

In some embodiments, the holes may have a circular shape and each hole may have an area of 1 mm² to 25 mm².

DETAILED DESCRIPTION OF THE DRAWINGS

Figure 1:
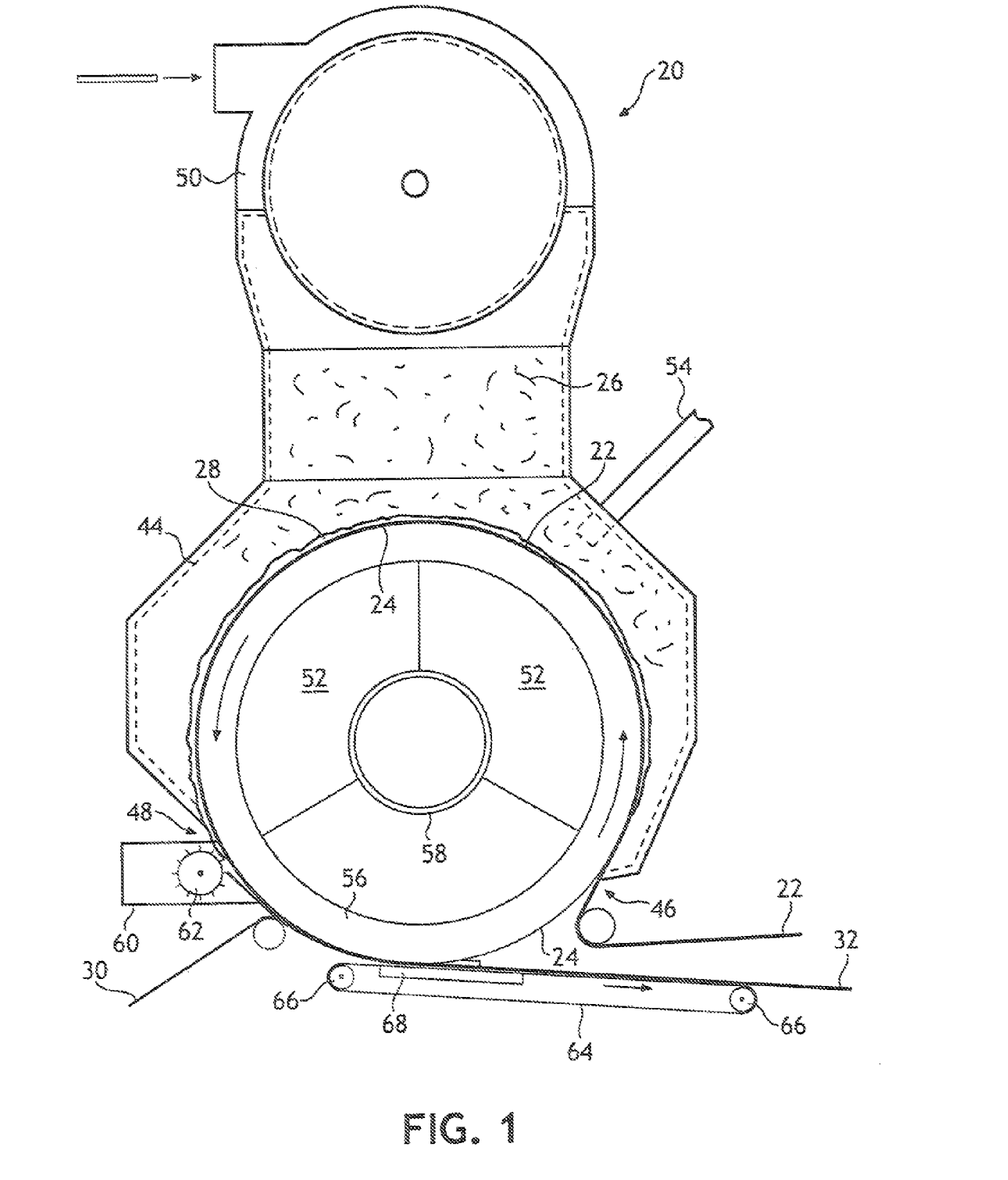
FIG. 1 representatively illustrates an exemplary method and apparatus of the present invention.

FIG. 1 representatively illustrates an exemplary method and apparatus of the present invention useful for forming absorbent composite webs. The absorbent composite webs of the present invention may be utilized in various absorbent articles, such as, for example, disposable diapers, adult incontinence articles, children's training pants, feminine hygiene articles, bandages, and the like.

One embodiment of the method of the present invention is illustrated generally at 20 and includes conforming a first web 22 onto a forming surface 24 having a plurality of nubs 34 (FIG. 2) protruding therefrom, depositing absorbent material 26 onto the first web 22 to form a unitary absorbent core web 28, and joining a second web 30 in facing relation with the first web 22 to form an absorbent composite web 32 wherein the absorbent core web 28 is located between the first web 22 and the second web 30.

The method 20 and apparatus of the invention can include a forming chamber 44 through which the forming surface 24 is movable. The forming chamber 44 has an appointed entrance portion 46, and an appointed exit portion 48. A fiber source, such as provided by a fiberizer 50, can be configured to provide fibrous material into the forming chamber 44, and a vacuum generator or other vacuum source can be configured to provide an operative, relatively lower pressure, vacuum condition in a vacuum-commutator duct system 52. In the illustrated configuration, the fiberizer 50 can be provided by a rotary hammer mill or a rotatable picker roll. Other fiberizers may also be employed, as desired.

As the forming surface 24 enters and then traverses through the forming chamber 44, the component materials of the absorbent core web 28, such as, the fibrous material, are operatively carried or transported by an entraining air stream that is drawn through the first web 22 and the forming surface 24. Typically, the low pressure, vacuum generating system is constructed and arranged to produce the desired airflow through the first web 22 and the forming surface 24. Such vacuum forming systems are well known in the art.

Other component materials for producing the absorbent core web 28 may also be delivered into the forming chamber 44. For example, particles or fibers of superabsorbent material may be introduced into the forming chamber 44 by employing conventional mechanisms, such as pipes, channels, spreaders, nozzles, and the like, as well as combinations thereof. In the representatively shown configuration, the superabsorbent material can be delivered into the forming chamber 44 by employing an operative conduit and nozzle system 54. The illustrated orientation of the delivery conduit 54 is exemplary, and it should be readily appreciated that any operative orientation of the delivery conduit and nozzle system 54 may be employed. The fibers, particles and other desired absorbent core materials may be entrained in any suitable gaseous medium.

The stream of air-entrained absorbent materials 26 can pass through the forming chamber 44 for deposition onto the first web 22 which overlies the forming surface 24. The forming chamber 44 can serve to direct and concentrate the air-entrained absorbent materials 26, and to provide a desired velocity profile in the air-entrained stream of absorbent materials 26. Typically, the forming chamber 44 is supported by suitable structural members, which together form a support frame for the forming chamber. The frame may be anchored and/or joined to other suitable structural components, as necessary or desirable.

The forming surface 24 can be provided by any suitable mechanism. In the representatively shown configuration, the forming surface 24 is provided by a forming drum 56. Other conventional techniques for providing the forming surface 24 may also be employed. For example, the forming surface 24 may be provided by an endless forming belt. Forming belt systems for producing fibrous webs are well known in the art. Examples of such forming belt systems are available from the Paper Converting Machine Company, a business having offices located in Green Bay, Wis., U.S.A.; and from Curt G. Joa Incorporated, a business having offices located in Sheboygan Falls, Wis., U.S.A.

In the representatively shown configuration, a forming drum system operatively provides the moving forming surface 24. More particularly, the moving foraminous forming surface 24 can be provided by an outer peripheral surface region of a rotatable forming drum 56. The forming drum 56 is rotatable in a selected direction of rotation, and can be rotated by employing a drum drive shaft that is operatively joined to any suitable drive mechanism (not shown). For example, the drive mechanism can include an electric or other motor which is directly or indirectly coupled to the drive shaft. While the shown arrangement provides a forming drum that is arranged to rotate in a counter-clockwise direction, it should be readily apparent that the forming drum may alternatively be arranged to rotate in a clockwise direction.

A suitable forming drum and forming system are taught in U.S. Pat. No. 6,630,096 to Venturino et al. issued Oct. 7, 2003, the entirety of which is incorporated herein by reference to the extent that it is consistent (i.e., not in conflict) herewith.

In the illustrated embodiment, under the influence of the vacuum generating source, a conveying air stream is drawn through the first web 22 and the foraminous forming surface 24 into the interior of the forming drum 56, and is subsequently passed out of the drum through the vacuum supply conduit 58. As the air-entrained absorbent materials 26 impinge on the first web 22, the air component is passed through the first web 22 and the forming surface 24 and the absorbent materials 26 are retained on the first web 22 to form a nonwoven unitary absorbent core web 28 thereon. The illustrated embodiments show a continuously formed unitary absorbent core web 28 formed on the first web 22. However, those skilled in the art will readily appreciate that discrete absorbent cores may alternatively be formed on the first web 22 such that a space exists between the absorbent cores. Therefore, where the term "absorbent core web" or "unitary absorbent core web" is used herein, the term "discrete absorbent core" or "discrete unitary absorbent core" is equally applicable in various embodiments. Suitable methods for forming discrete absorbent cores are disclosed in U.S. patent application Ser. No. 11/215,876 to Wisneski et al. entitled "Method and Apparatus for Making Absorbent Article With Core Wrap" and filed on Aug. 30, 2005, the entirety of which is incorporated herein by reference to the extent that it is consistent (i.e., not in conflict) herewith.

Optionally, a scarfing system may be positioned at the exit region 48 of the forming chamber 44. The scarfing system can include a scarfing chamber 60 and a scarfing roll 62 which is positioned within the scarfing chamber. The scarfing roll can abrade excess absorbent material 26 from the absorbent core web 28, and the removed fibers can be transported away from the scarfing chamber 60 with a suitable discharge conduit, as is well known in the art. The removed absorbent material 26 may, for example, be recycled back into the forming chamber 44 or the fiberizer 50, as desired. Additionally, the scarfing roll can rearrange and redistribute the web material along the longitudinal machine-direction of the web and/or along the lateral cross-direction of the web.

The rotatable scarfing roll may be operatively connected and joined to a suitable shaft member, and may be driven by a suitable drive system (not shown). The scarfing roll system can provide a conventional trimming mechanism for removing or redistributing any excess, z-directional thickness of the absorbent core web 28 that has been deposited on the first web 22. The surface of the scarfing roll can be adjusted to provide a desired contour along the scarfed surface of the absorbent core web 28. The scarfing roll can, for example, be configured to provide a substantially flat surface along the scarfed surface of the absorbent core web 28. The scarfing roll can optionally be configured to provide a non-flat surface. The scarfing roll 62 is disposed in spaced adjacent relationship to the forming surface 24, and the forming surface 24 is translated past the scarfing roll. A conventional transporting mechanism, such as a suction fan (not shown) can draw the removed fibrous material away from the formed absorbent core web 28 and out from the scarfing chamber 60.

The scarfing roll 62 may be rotated in a direction which moves a contacting surface of the scarfing roll in a counter-direction that is opposite the movement direction of the absorbent core web 28. Alternatively, the scarfing roll 62 may be rotated in a co-direction that is the same as the movement direction of absorbent core web 28. In either situation, the rotational speed of the scarfing roll 62 should be suitably selected to provide an effective scarfing action against the contacted surface of the formed absorbent core web 28. In like manner, any other suitable trimming mechanism may be employed in place of the scarfing roll assembly to provide a cutting or abrading action to the laid fibrous web by a relative movement between the fibrous web and the selected trimming mechanism. A suitable scarfing system is taught in U.S. Pat. No. 6,627,130 to Kugler et al. issued Sep. 30, 2003, the entirety of which is incorporated herein by reference to the extent that it is consistent (i.e., not in conflict) herewith.

After formation of the absorbent core web 28, the second web 30 is overlaid upon the absorbent core web 28 and the first web 22 while both are conformed to the forming surface 24 and the nubs 34 (FIG. 2) protruding therefrom. The second web 30 is then joined to the first web 22 while still conformed to the forming surface 24 and the nubs 34 to form the completed absorbent composite web 32. Subsequently, with the rotation of the drum, the formed absorbent composite web 32 can be removed from the forming surface 24. The removal operation may be provided by the weight of the absorbent composite web 32, by centrifugal force, by a positive air pressure, or by combinations thereof. The positive air pressure can be produced, for example, by a source of compressed air or a fan which generates a pressurized air flow that exerts a force directed outwardly through the forming surface.

The portion of the forming surface 24 that is carrying the absorbent composite web 32 can be moved to an optional pressure blow-off zone of the forming drum system. In the blow-off zone, air can be introduced under pressure and directed radially outwardly against absorbent composite web 32 on the portion of the forming surface that becomes aligned with the blow-off zone. The gas pressure can effect a ready release of the absorbent composite web 32 from the forming surface 24, and the absorbent composite web 32 can be removed from the forming surface onto a suitable transport mechanism.

A web transporter can receive the absorbent composite web 32 from the forming drum 56, and convey the absorbent composite web 32 for further processing. In various embodiments, portions the absorbent composite web 32, such as the first web 22 and/or the second web 30, may be folded to seal the edges of the absorbent core web 28.

Suitable web transporters can, for example, include conveyer belts, vacuum drums, transport rollers, electromagnetic suspension conveyors, fluid suspension conveyors, or the like, as well as combinations thereof. As representatively shown, the web transporter can be provided by a system which includes the illustrated endless conveyor belt 64 disposed about rollers 66. In a particular configuration of the invention, a vacuum suction box 68 can be located below the conveyor belt 64 to help remove the absorbent composite web 32 from the forming surface 24. The vacuum box 68 opens onto the belt 64, and a suction of air out of the vacuum box can draw an air flow through perforations in the conveyor belt. This flow of air can, in turn, operate to draw the absorbent composite web 32 away from the forming surface. The vacuum box can be employed with or without the use of a positive pressure in the blow-off zone.

Figure 2:
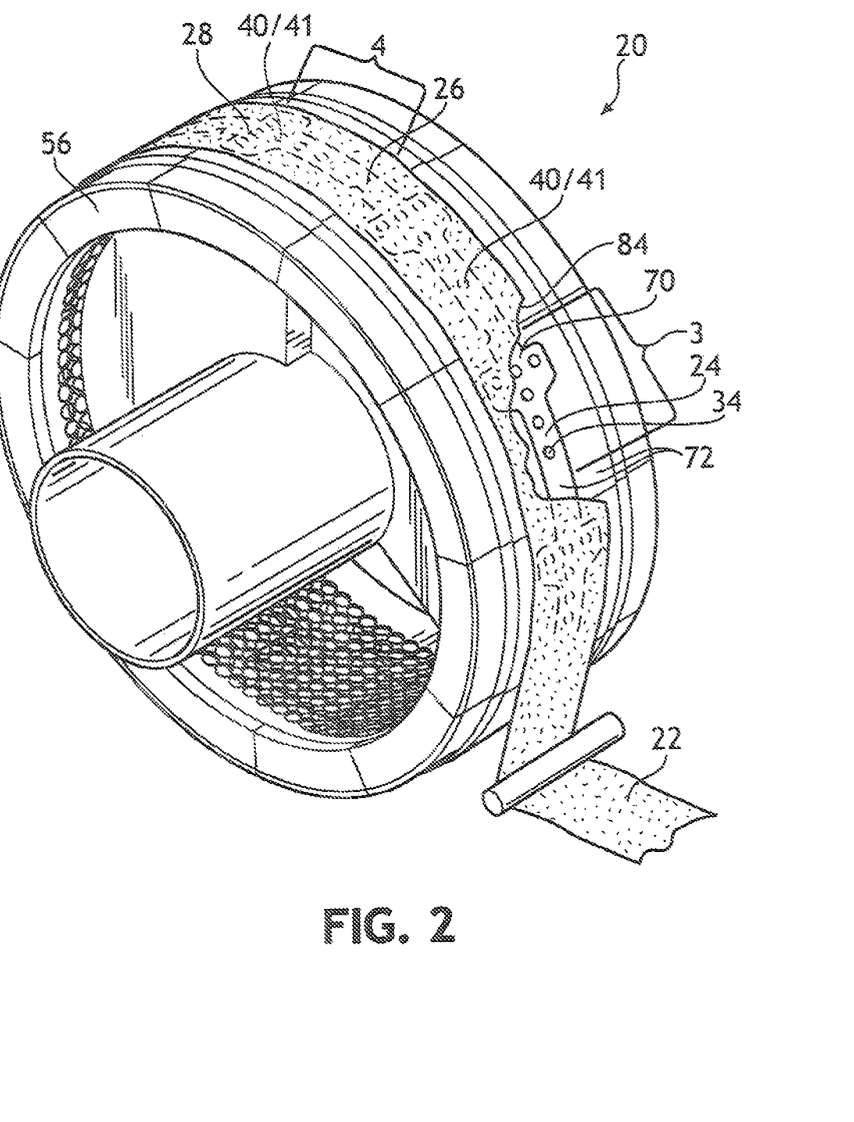
FIG. 2 representatively illustrates a perspective view of a portion of an exemplary method and apparatus of the present invention.

With reference to FIG. 2, the forming surface 24 can be provided along the outer, cylindrical surface of the forming drum 56, and can extend along the axial (cross-directional) and circumferential (machine-directional) dimensions of the forming drum. The structure of the forming surface 24 can be composed of an assembly, and can include a foraminous or otherwise porous member 70 which is operatively connected and joined to the forming drum 56.

The porous forming member 70 can extend along the outer, circumferential periphery of the forming drum 56. The forming member 70 can be composed of any suitable porous material. The foraminous member 70 may include a screen, a wire mesh, a hard-wire cloth, a perforated member, or the like, as well as combinations thereof. In a particular aspect, the foraminous member can include a fluted member having open channels which can extend generally radially and can allow a substantially free flow of air or other selected gas from the outward-side of the drum towards the center of the drum. The flutes or channels can have any desired cross-sectional shape, such as circular, oval, hexagonal, pentagonal, other polygonal shape, or the like, as well as combinations thereof. Such honeycomb structures are well known in the art, and can be composed of various materials, such as plastic, metal, ceramics, and the like, as well as combinations thereof. For example, suitable materials and structures are available from Innovent, a business having offices located in Peabody, Mass., U.S.A.

In various embodiments, the radially outward surface of the fluted member or other foraminous member 70 can be configured with a selected surface contour. The contoured surface regions of the foraminous member 70 can be formed to have any operative shape. In various arrangements, the contour shape can be trapezoidal. Alternatively, the contour shape can be domed or flat.

The forming surface 24, and particularly the porous member 70, can include a forming surface contour which is uniform or non-uniform along its depth dimension. For example, the forming surface 24 can provide a relatively low-basis-weight region, and at least one relatively high-basis-weight region, such as provided by pocket regions. In various embodiments, at least one relatively high basis weight region can be positioned along a medial region of the forming surface 24. Alternatively, at least one relatively high basis weight region can be positioned along one or more other, non-medial regions of the forming surface 24.

With reference to FIGS. 2, 3, 5 and 6, at least one side-masking member, such as provided by a side contour ring 72 can be disposed on the foraminous member 70. In various embodiments, the invention can include a cooperating system of side-masking members. As representatively shown, a pair of laterally opposed, side contour ring members 72 can be configured to extend circumferentially around the forming drum 56. In a particular aspect, the contour rings 72 can be operatively attached and positioned along laterally opposed, outboard edge regions of the foraminous member 70. The contour rings 72 can be joined and assembled to the forming surface 24 by employing conventional attaching or mounting mechanisms.

Figure 3:
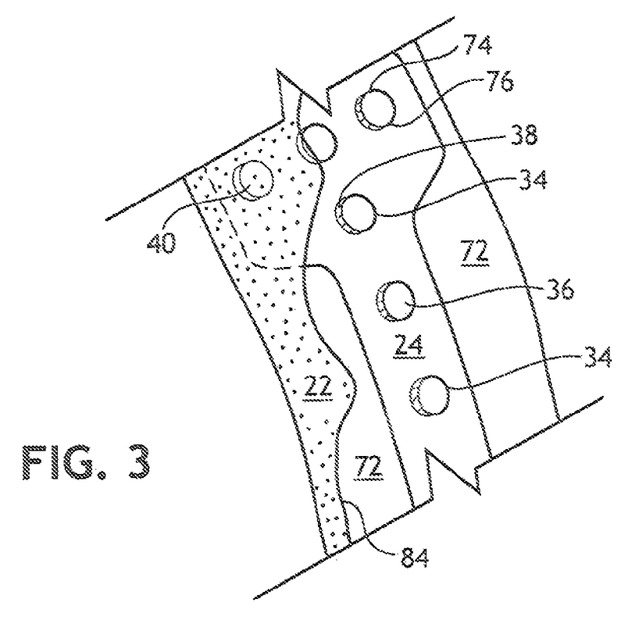
FIG. 3 representatively illustrates a portion of FIG. 2 designated by bracket 3.
Figure 4:
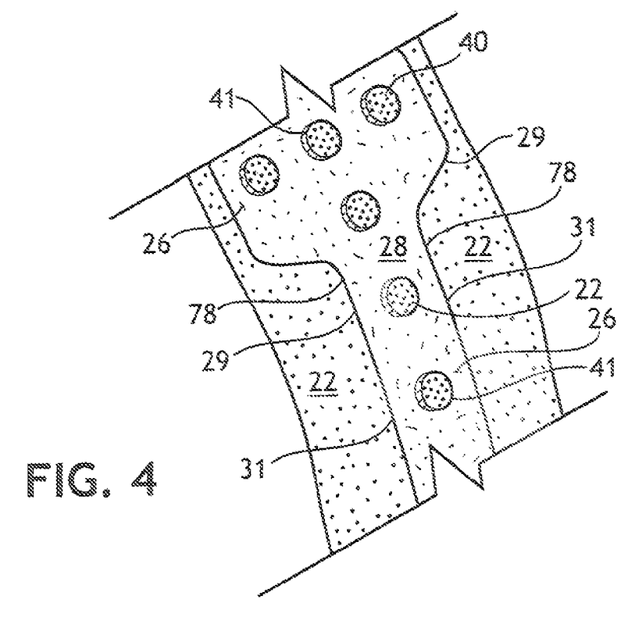
FIG. 4 representatively illustrates a portion of FIG. 2 designated by bracket 4.

FIG. 2 representatively illustrates a perspective view of the first web 22 conforming to a forming surface 24 with portions of the absorbent material 26 and portions of the first web 22 cut away along line 84 to illustrate underlying details. FIG. 3 representatively illustrates a more detailed view of the portion of FIG. 2 designated by bracket 3 with the absorbent material 26 removed to illustrate underlying details. FIG. 4 representatively illustrates a more detailed view of the portion of FIG. 2 designated by bracket 4.

Referring now to FIGS. 2 and 3, the forming surface 24 includes a plurality of raised nubs 34 having upper surfaces 36. In various embodiments, the raised nubs 34 may also have side surfaces 38. The first web 22 is conformed about the forming surface 24 and the plurality of nubs 34. The first web 22 may be drawn down to the forming surface 24 and around the nubs 34 via vacuum forces or the like. The first web 22 overlies the forming surface 24 and the nubs 34 and defines a plurality of bonding areas 40. The bonding areas 40 correspond to those portions of the first web 22 overlying the upper surfaces 36 of the nubs 34.

As used herein, the terms "conform," "conforming," or derivatives thereof mean to give the same shape, outline, or contour to. For example, when the first web 22 is "conformed" to the forming surface 24, the first web 22 is generally in contact with most of the forming surface 24 and at least the upper surfaces 36 of the nubs 34. See FIG. 6 for an example of the first web 22 conforming to the forming surface 24 and the nubs 34.

The nubs 34 may be formed out of a wide variety of different materials. For example, the nubs 34 may be formed out of plastic, metal, ceramin, or the like, or combinations thereof. Metallic nubs are advantageous because they are durable and have a relatively low coefficient of friction. An aluminum nub provided with polytetrafluorethylene or other suitable release coating can be used to provide a durable and low friction nub.

The nubs 34 may be attached to the forming surface 24 by using any suitable means such as, for example, fasteners, welding, adhesives, and the like, and combinations thereof. Alternatively, the nubs 34 may be formed integrally with the forming surface 24. In various embodiments, the nubs 34 may be the heads of various fasteners, such as, for example, bolts or screws, or the like, having any suitable head, such as, hex heads, button heads, socket heads, cap heads, or the like, or combinations thereof. For example, in some embodiments, the nubs 34 may be bolts secured to the forming surface 24. The nubs 34 are illustrated as lying within the interior region of the forming surface whereby the nubs 34 will be completely circumscribed by the absorbent material 26 deposited on the first web 22 overlying the forming surface 24. However, in various embodiments, the nubs 34 may be located at the edges of the forming surface whereby only a portion of one or more nubs 34 may be circumscribed by the absorbent material 26.

The illustrated nubs 34 do not include perforations or apertures on either the side surfaces 38 or upper surfaces 36 of the nub 34 and, thus, process air is not pulled directly through the illustrated nubs 34. It would be possible, however, for the nubs to include such openings on the side surface 38 to allow the process air to be removed there though in addition to the remainder of the forming surface 24.

In various embodiments, the surface area of any individual nub 34 may be 1 mm$^2$ (0.0015 in$^2$) to 200 mm$^2$ (0.3 in$^2$), 1 mm$^2$ (0.0015 in$^2$) to 100 mm$^2$ (0.155 in$^2$), or 1 mm$^2$ (0.0015 in$^2$) to 25 mm$^2$ (0.03875 in$^2$). In some embodiments, the surface area of any individual nub 34 may be less than 200 mm$^2$, less than 100 mm$^2$, less than 90 mm$^2$, less than 80 mm$^2$, less than 70 mm$^2$, less than 60 mm$^2$, less than 50 mm$^2$, less than 40 mm$^2$, less than 30 mm$^2$, less than 20 mm$^2$, or less than 10 mm$^2$. In various embodiments, the total nub-surface area may be between about 1 to about 33 percent, about 1 to about 25 percent, or less than about 10 percent of the total forming surface area. As used herein, the total nub surface area is the combined cross sectional area of the nubs at the base of the nubs where the nubs are attached to the forming surface. The total forming surface area includes the area of the forming surface on which the absorbent material is deposited plus the total nub surface area.

In various embodiments, the nubs 34 may have any suitable height. The nub height represents the perpendicular distance that the upper surface 36 of the nubs 34 extends from the forming surface 24. In various embodiments, the nubs 34 may have a height less than 10, less than 9, less than 8, less than 7, less than 6, less than 5, less than 4, less than 3, or less than 2 mm. In some embodiments, the nubs 34 may have a height of 1 mm to 10 mm, 1 mm to 7 mm, or 1.5 mm to 6 mm.

The nubs 34 may have a variety of different shapes and/or configurations. For example, the cross section of the nubs 34 may define a circle, oval, star, diamond, rectangle, or any other geometric figure. In some embodiments, the nubs 34 may have an irregular cross sectional shape or may be generally linear or arcuate. Furthermore, the cross sectional shape of the nubs 34 may vary over the height of the nubs 34. For example, the nubs 34 may be provided with a slight taper whereby the upper surface 36 of the nub 34 has an area which is less than the cross sectional area of the base of the nub at the point where the nub is attached to the forming surface 24. The inward taper of the side surfaces 38 may be in the range of between 0° to about 15°. For example, side surfaces may have an inward taper of approximately 5° or 7°.

Alternatively, the side surfaces 38 of the nubs 34 may be perpendicular to the forming surface 24, pitched slightly outward, or vary over the perimeter or height of the nub 34. For example, a nub 34 could have a leading edge 74 which is perpendicular to the forming surface and a trailing edge 76 which is pitched slightly inward and thus have a pitch which varies over the perimeter of the nub 34. A nub 34 which is perpendicular near its base (i.e., has a 0° taper) but tapers inwardly near its distal end would have a pitch which varies over the height of the nub 34. Thus, the nubs 34 may take a variety of different shapes. The configuration of the nubs 34, however, must account for the interaction of the nub 34 and the first web 22 and the absorbent core web 28.

In some embodiments, the nubs 34 may have a circular shape. The nubs 34 may have a diameter of 1 mm to 16 mm, 1 mm to 10 mm, or 1 mm to 5 mm. In some embodiments the nubs 34 may have a diameter of less than 16 mm, less than 10 mm, or less than 5 mm. The pattern formed by the nubs 34 on the forming surface 24 may be varied significantly.

Referring now to FIGS. 2 and 4, the method 20 further includes depositing absorbent material 26 onto the first web 22 to form a unitary absorbent core web 28 having a plurality of holes 41 formed therein. The absorbent material 26 surrounds the bonding areas 40 which overlie the nubs 36 thereby defining the holes 41. The unitary absorbent core web 28 defines lateral side edges 31. In embodiments with discrete absorbent cores, the discrete absorbent cores further define longitudinal end edges 80 (see FIG. 9). In various embodiments, the bonding areas 40 of the first web 22 are free of absorbent material 26 or substantially free of absorbent material 26. In various embodiments, the bonding areas 40 may include some absorbent material 26 that is removed prior to subsequent processing. In some embodiments, the scarfing roll 62 can optionally be configured to remove most or all deposited absorbent material 26 from the bonding areas 40 of the first web 22.

As used herein, the term "unitary" means "undivided" and describes an absorbent core wherein no portion of the absorbent core is completely disconnected from any other portion. The unitary absorbent core includes a plurality of holes wherein a first sheet and a second sheet are bonded together through the plurality of holes to form an absorbent composite. In other words, a unitary absorbent core is a "sea" of absorbent material with "islands" of bond points. In contrast, some prior art absorbent cores formed discrete pockets of absorbent material encapsulated between sheets that were connected together between the pockets to create a "sea" of bond areas with "islands" of absorbent material.

Unitary absorbent cores can be formed discretely or can be formed as webs. As used herein, the term "unitary absorbent core web" describes a series of unitary absorbent cores directly connected together to form a web. As used herein, the term "discrete unitary absorbent core" describes a unitary absorbent core that is formed such that it is not directly connected to another unitary absorbent core.

Figure 5:
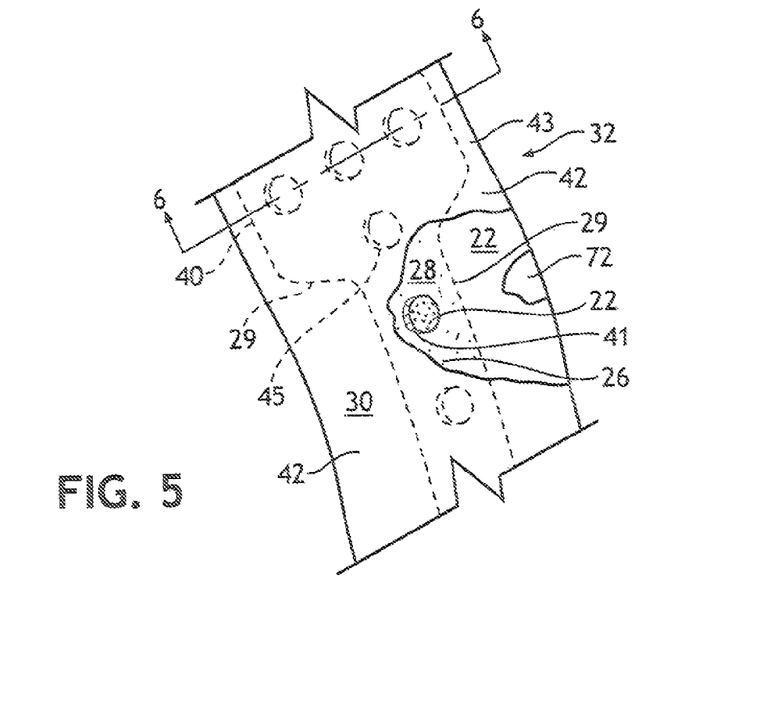
FIG. 5 representatively illustrates a portion of the method and apparatus of the present invention.

The method 20 further includes joining a second web 30 to the first web 22 on upper surfaces 36 of the nubs 34 to form an absorbent composite web 32 upon the forming surface 24. FIG. 5 representatively illustrates a portion of the method 20 not seen in FIG. 2 wherein the second web 30 is joined in facing relation to the first web 22 at bond points 45 to form the absorbent composite web 32. The bond points 45 correspond to the bonding areas 40 of the first web 22. In various embodiments, the second web 30 may additionally be joined to the first web 22 at marginal areas 42. The marginal areas 42 are defined as the areas outboard of the absorbent core lateral side edges 78 and the longitudinal end edges 80.

As used herein, the use of the term "join," "joined," "joining," or variations thereof in describing the relationship between two elements means that the two elements can be connected together by heat sealing, ultrasonic bonding, adhesive bonding, thermal bonding, pressure bonding, stitching, or the like, or combinations thereof. Further, the two elements can be joined directly together (i.e., touching), or may have one or more elements interposed between them, all of which are suitably connected together.

Figure 9:
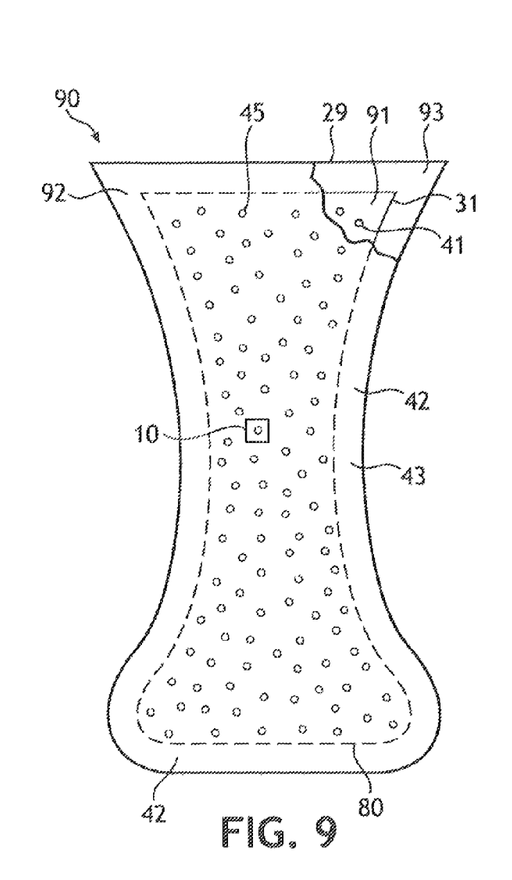
FIG. 9 representatively illustrates an exemplary absorbent composite of the present invention.

In the illustrated embodiments, the absorbent core web 28 is formed as a continuous web and therefore the marginal areas 42 extend beyond the lateral side edges 78 of the absorbent core web 28. However, those skilled in the art will readily appreciate that discrete absorbent cores may be formed such that a space exists between subsequent absorbent cores. As such, the marginal areas 42 may therefore extend around the entire perimeter 29 of the absorbent core (FIG. 9). Suitable methods for forming discrete absorbent cores is disclosed in U.S. patent application Ser. No. 11/215,876 to Wisneski et al. entitled "Method and Apparatus for Making Absorbent Article With Core Wrap" and filed on Aug. 30, 2005, the entirety of which is incorporated herein by reference to the extent that it is consistent (i.e., not in conflict) herewith.

Figure 6:
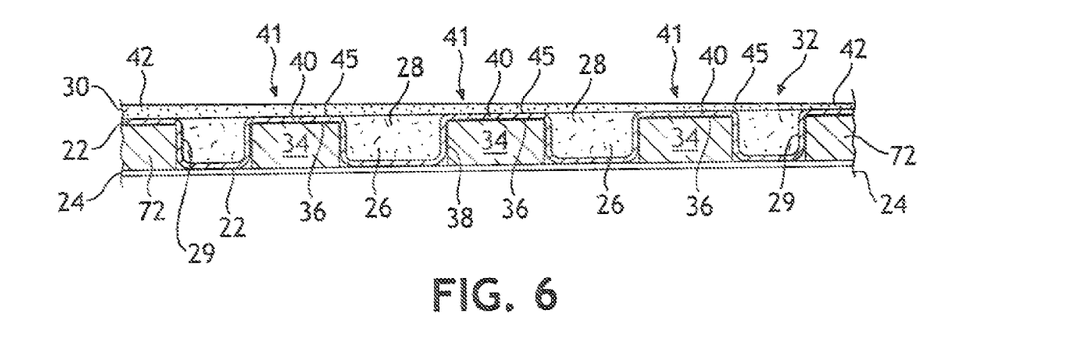
FIG. 6 representatively illustrates a cross-sectional view of the method and apparatus of FIG. 5 taken along the line 6-6.

FIG. 6 representatively illustrates a cross sectional view of the absorbent composite web 32 on the forming surface 24 taken along the line 6-6 of FIG. 5. The first web 22 is conformed to the forming surface 24 and overlays the nubs 34 and the side contour rings 72 at the marginal area 42. The portions of the first web 22 overlying the upper surfaces 36 of the nubs 34 define the bonding areas 40. The absorbent material 26 is formed upon the first web 22 and surrounds the nubs 34 to form the unitary absorbent core web 28 having holes 41 therein. The holes 41 are defined by the nubs 34. The bonding areas 40 of the first web 22 are exposed within the holes 41. The absorbent core web 28 also includes a perimeter 29 defined in part by the side contour rings 72. The second web 30 is overlaid on the first web 22 and the unitary absorbent core web 28. The second web 30 is joined to the first web 22 at the bonding areas 40 to form bond points 45. The second web 30 may also be joined to the first web 22 at the marginal areas 42. Therefore, the absorbent composite web 32 is stabilized because the first web 22 and the second web 30 are joined together at bond points 45 which extend through holes 41 in the absorbent core web 28 located between the first web 22 and the second web 30.

The second web 30 may be joined to the first web 22 by any suitable means to form the absorbent composite web 32. In various embodiments, the second web 30 may be joined to the first web 22 at the bonding areas 40 and/or the marginal areas 42 by adhesive bonding, ultrasonic bonding, thermal bonding, pressure bonding, and the like, and combinations thereof to form the absorbent composite web 32. The joining at the bonding areas 40 results in bond points 45.

In some embodiments, the second web 30 may be joined to the first web 22 by applying adhesive to the second web 30 before overlying the second web 30 in facing relation with the first Web 22 and the unitary absorbent core web 28. The second web 30 may then be directly joined to the bonding areas 40 of the first web 22 via the adhesive to form the absorbent composite web 32 having bond points 45. In various embodiments, the adhesive may be applied to the first web 22 and/or the second web 30 in any suitable pattern or covering any suitable surface area. For example, the adhesive pattern may include meltblown, swirl, slot coat, beads, or the like, or combinations thereof. The adhesive may be applied across at least 50 percent, at least 60 percent, at least 70 percent, at least 80 percent, or at least 90 percent of the surface area of the first web 22 and/or the second web 30. The adhesive is preferably applied to at least those portions of the second web 30 that align with the bonding areas 40 of the first web 22 to effectuate the joining of the webs 22 and 30 at the bonding areas 40 to form the bond points 45.

In various embodiments, adhesive may be applied to the first web 22, the second web 30, or both the first web 22 and the second web 30 before the second web 30 is overlaid upon the absorbent core web 28 and the first web 22. In various embodiments, the second web 30 may be pressed against the bonding areas 40 to effectuate a stronger joining at the bond points 45 between the first web 22 and the second web 30 while on the forming surface 24.

In various embodiments, the second web 30 may be joined to the first web 22 at the marginal areas 42 to define a flange 43. The flange 43 may extend beyond the perimeter 29 of the unitary absorbent core web 28 by any suitable distance. The flange 43 may be subsequently cut by any suitable means into any suitable shape and suitable contour. For example, in some embodiments, the flange 43 may be cut using a die cutter, high pressure water cutter, or the like, and may be shaped to follow the lateral side edges 78 of the unitary absorbent core web 28. In some embodiments, including the forming of discrete absorbent cores, the flange 43 may be generally shaped to follow the entire perimeter 29 of the discrete absorbent core (FIG. 9).

In some embodiments, the marginal areas 42 of the first web 22 may be folded around the absorbent core web 28 and joined to the second web 30 to seal the lateral edges 78 of the absorbent core web 28. In some embodiments, the marginal areas 42 of the second web 30 may be folded around the absorbent core web 28 and joined to the first web 22 to seal the lateral edges 78 of the absorbent core web 28. In some embodiments, the flange 43 formed by the first web 22 and the second web 30 may be folded around the absorbent core web 28 and joined to first web 22 and/or the second web 30. Any suitable means may be used to fold the first web 22, the second web 30, and/or the flange 43. For example, conventional folding boards, and the like, may be used. Suitable folding methods and apparatus are disclosed in U.S. patent application Ser. No. 10/955,820 to Mischler et al., filed on Sep. 30, 2004, the entirety of which is incorporated herein by reference to the extent that it is consistent (i.e., not in conflict) herewith The present invention advantageously forms holes 41 in the absorbent core web 28 around the bonding areas 40. The first web 22 and the second web 30 are joined together through the holes 41 at the bonding areas 40 to form bond points 45 while the first web 22 is conformed about the nubs 34 and the absorbent core web 28 is formed about the nubs 34 thereby ensuring registration between the bonding areas 40 and the holes 41. Furthermore, having both the hole formation step and the bonding step occur on the same forming surface 24 allows the size of the hole 41 to be very similar to the size of the bond point 45 in the bonding area 40 because both are created by the same nub 34 while still engaged with the nub 34. In other words, the bond points 45 cannot get out of registration with the holes 41.

In some embodiments, the first web 22 may provide the functions of both the first web 22 and the second web 30. For example, the first web 22 may define a forming section and a wrap section. The first web 22 may be provided at a width substantially wider than the width of the absorbent core web 28. The absorbent core web 28 may be formed on the forming section of the first web 22 as described herein and the wrap section of the first web 22 may be folded and overlaid upon the absorbent core web 28 and joined to the forming section as described herein to create the absorbent composite web 32.

In various embodiments, the absorbent composite web 32 may be compressed or densified by any suitable means, such as, for example, passing the absorbent composite web 32 through a fixed gap nip commonly referred to as debulking. Debulking the absorbent composite web 32 compresses and expands the unitary absorbent core web 28 and reduces the size of the holes 41. Therefore, the size of the holes 41 approaches the size of the bond points 45 and results in minimally oversized holes 41 as compared to the bond points 45.

In various embodiments, the first web 22 may be a tissue web, the second web 30 may be a tissue web, and the second web 30 may be joined to the first web 22 at the bonding areas 40 to form bond points 45 with adhesive or any other suitable means.

In various embodiments, the first web 22 may be a non-woven web, the second web 30 may be a nonwoven web, and the second web 30 may be joined to the first web 22 at the bonding areas 40 to form bond points 45 by adhesive bonding, ultrasonic bonding, pressure bonding, thermal bonding, or the like, or combinations thereof.

In various embodiments, the first web 22 and the second web 30 may be provided by a similar material. Alternatively the first web 22 and the second web 30 may be provided by dissimilar materials. The first web 22 may be adapted to face a user's body during use, and the second web 30 may be adapted to face away from the user's body during use or the first web 22 may be adapted to face away from a user's body during use, and the second web 30 may be adapted to face the user's body during use.

Various woven and nonwoven fabrics may comprise the first web 22 and/or the second web 30. For example, the first web 22 and/or the second web 30 may be composed of a meltblown or spunbonded web of polyolefin fibers. The first web 22 and/or the second web 30 may also be a bonded-carded web composed of natural and/or synthetic fibers. The first web 22 and/or the second web 30 may be composed of a substantially hydrophobic material, and the hydrophobic material may, optionally, be treated with a surfactant, or otherwise processed, to impart a desired level of wettability and hydrophilicity. Specifically, the first web 22 and/or the second web 30 may be a nonwoven, spunbond-meltblown-spunbond, polypropylene fabric having a basis weight of about 5 to 30 gsm.

The first web 22 and/or the second web 30 may be stretchable, either elastically or extensibly, thereby allowing the absorbent core web 28 to swell. The first web 22 and the second web 30 may suitably be composed of a material which is either liquid permeable or liquid impermeable. It is generally desirable that at least one of the first web 22 and the second web 30 be formed from a material which is substantially liquid permeable. The liquid permeability may be inherent in the first web 22 and/or the second web 30, such as in the example of a low basis weight spunbond. Alternatively, the permeability may result from the first web 22 and/or the second web 30 that is inherently liquid impermeable, such as in the example of a film, which has been modified to provide the permeability, for example by aperturing.

Other suitable materials for the first web 22 and/or the second web 30 are described in commonly assigned U.S. patent application Ser. No. 11/020,842 to Abuto et al., entitled, "Stretchable Absorbent Core and Wrap," filed Dec. 21, 2004, the entirety of which is incorporated herein by reference to the extent that it is consistent (i.e., not in conflict) herewith. The first web 22 and/or the second web 30 may be manufactured by any suitable means, such as, for example the processes described in U.S. Pat. No. 5,458,592 to Abuto et al. and issued Oct. 17, 1995, the entirety of which is incorporated herein by reference to the extent that it is consistent (i.e., not in conflict) herewith.

In some embodiments, the absorbent composite web 32 may be separated into discrete absorbent composites 90 by any suitable means, such as, for example, rotary cutters, high pressure water cutters, die cutters, saw cutters, and the like. The separation of the absorbent composite web 32 into discrete absorbent composites 90 includes the separation of the first web 22 into discrete first sheets 92 and the second web 30 into discrete second sheets 93. As discussed herein, the absorbent core may be formed as a continuous absorbent core web 28 and cut into discrete absorbent cores 91 or may be formed as discrete absorbent cores 91. Therefore, the separation of the absorbent composite web 32 into discrete absorbent composites 90 may or may not require the separation of the absorbent core web 28 into discrete absorbent cores 91.

Figure 7:
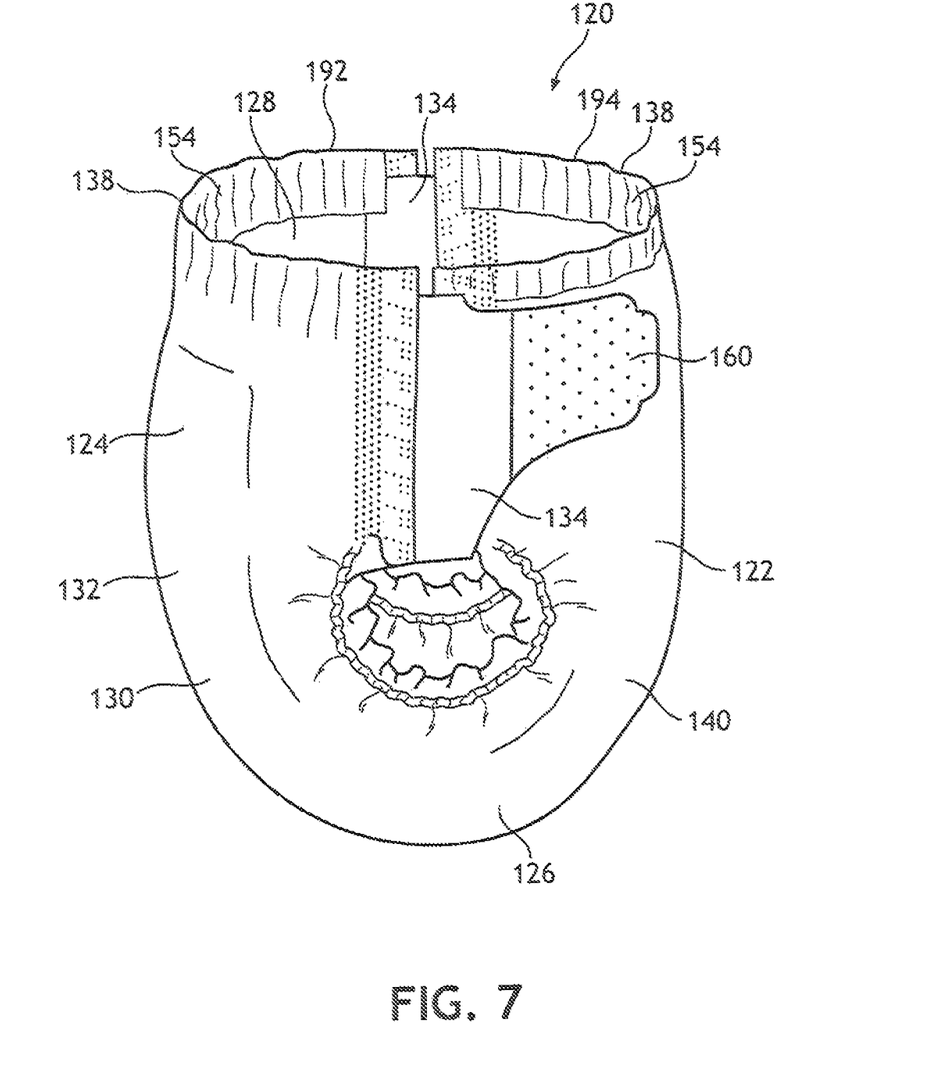
FIG. 7 representatively illustrates an exemplary absorbent article of the present invention.
Figure 8:
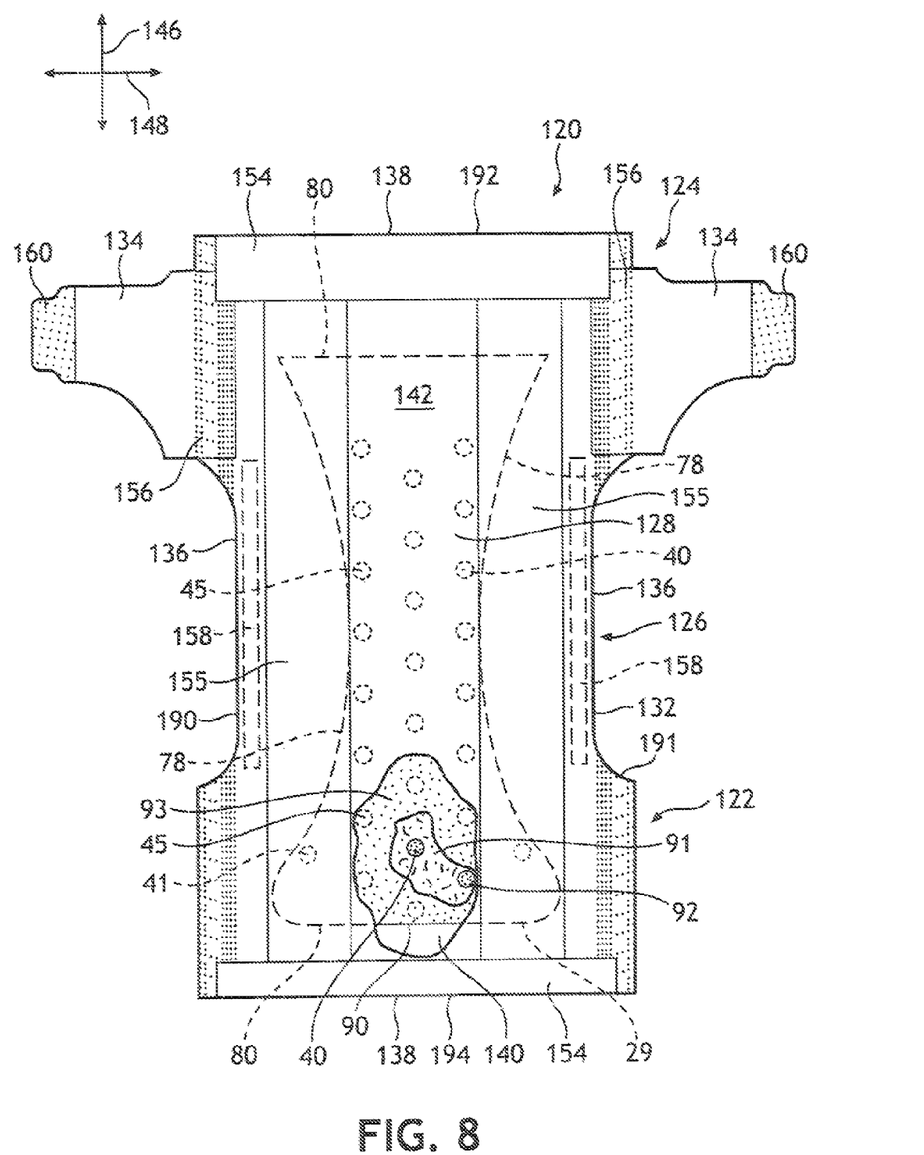
FIG. 8 representatively illustrates the absorbent article of FIG. 7 in the laid flat condition with the side contacting the wearer facing the viewer.

Referring now to FIGS. 7 and 8, the discrete absorbent composite 90 of the present invention is representatively illustrated as part of a baby diaper. The baby diaper is indicated in its entirety by the reference numeral 120. The diaper 120 can suitably be disposable, which refers to articles that are intended to be discarded after a limited period of use instead of being laundered or otherwise conditioned for reuse. It should also be understood that the absorbent composite 90 of the present invention is suitable for use with various other absorbent articles intended for personal wear, including, but not limited to, children's training pants, feminine hygiene products, incontinence products, medical garments, surgical pads and bandages, other personal care or health care garments, and the like, without departing from the scope of the present invention.

By way of illustration only, various materials and methods for constructing diapers such as the diapers 120 of the various aspects of the present invention are disclosed in U.S. patent application Ser. No. 10/836,490, filed Apr. 29, 2004, in the name of Schlinz et al.; U.S. Pat. No. 5,496,298 issued Mar. 5, 1996, to Kuepper et al.; U.S. Pat. No. 4,798,603 issued Jan. 17, 1989, to Meyer et al.; U.S. Pat. No. 5,176,668 issued Jan. 5, 1993, to Bernardin; U.S. Pat. No. 5,192,606 issued Mar. 9, 1993, to Proxmire et al., and U.S. Pat. No. 5,509,915 issued Apr. 23, 1996, to Hanson et al., each of which are incorporated herein by reference to the extent that they are consistent (i.e., not in conflict) herewith.

The diaper 120 is illustrated in FIG. 7 in a fastened condition. The diaper 120 is illustrated in FIG. 8 in a laid flat and unfastened condition with portions cut away to illustrate underlying detail. The diaper 120 defines a longitudinal direction 146 and a lateral direction 148 perpendicular to the longitudinal direction as shown in FIG. 8. The diaper 120 further defines a pair of longitudinal end regions, otherwise referred to herein as a front waist region 122 and a back waist region 124, and a center region, otherwise referred to herein as a crotch region 126, extending longitudinally between and interconnecting the front and back waist regions 122, 124. The front and back waist regions 122, 124 include those portions of the diaper 120, which, when worn, wholly or partially cover or encircle the waist or mid-lower torso of the wearer. The crotch region 126 generally is that portion of the diaper 120 which, when worn, is positioned between the legs of the wearer and covers the lower torso and crotch of the wearer. The diaper 120 also defines an inner surface 128 adapted to be positioned toward the wearer, and an outer surface 130 opposite the inner surface. With additional reference to FIG. 8, the diaper 120 has a pair of opposed article side edges 136 extending in the longitudinal direction 146 and a pair of opposed article waist edges 138 extending in the lateral direction 148, referred to herein as the article back waist edge and the article front waist edge.

The illustrated diaper 120 can include an absorbent chassis, generally indicated at 132. The absorbent chassis 132 can define a first chassis side edge 190 extending in the longitudinal direction 146 and a second chassis side edge 191 extending in the longitudinal direction 146, opposite the first chassis side edge 190. The absorbent chassis 132 can also define a pair of longitudinally opposite chassis waist edges referred to herein as the chassis back waist edge 192 and the chassis front waist edge 194.

For example, in the aspect of FIGS. 7 and 8, the diaper 120 includes an absorbent chassis 132 and a pair of ears 134 formed separately from and attached to the absorbent chassis 132 proximate the first chassis side edge 190 and the second chassis side edge 191. The ears 134 can be attached along seams 156 proximate the chassis side edges 190, 191 in either the front waist region 122 or in the back waist region 124 of the diaper 120. In the illustrated aspects, the ears 134 are attached in the back waist region 124. The ears 134 may be attached to the absorbent chassis 132 using means known to those skilled in the art such as adhesive, thermal bonding, pressure bonding, ultrasonic bonding, and the like, or combinations thereof. In alternative embodiments, the ears 134 may be formed as an integral part of the absorbent chassis 132. The ears 134 may also include fasteners 160, as are known in the art, adapted to releasably secure the diaper 120 about the waist of the wearer.

The absorbent chassis 132 is illustrated in FIG. 8 as being substantially I-shaped. However, it is contemplated that the absorbent chassis 132 may have other shapes (e.g., hourglass, T-shaped, rectangular, and the like) without departing from the scope of this invention.

The absorbent chassis 132 can include an outercover 140 and a bodyside liner 142 in a superposed relation therewith. The liner 142 can be suitably joined to the outercover 140 along at least a portion of the absorbent chassis 132. The liner 142 can be suitably adapted, i.e., positioned relative to the other components of the diaper 120, to contact the wearer's skin during wear of the diaper. The absorbent chassis 132 may also include the absorbent composite 90 disposed on the inner surface of the article relative to the outercover 140 for absorbing liquid body exudates. For example, the absorbent composite 90 can be located between the outercover 140 and the bodyside liner 142. The bodyside liner 142 and the outercover 140 can be attached to each other by adhesive, ultrasonic bonding, thermal bonding or by other suitable attachment techniques known in the art. Moreover, at least a portion of the absorbent composite 90 can optionally be attached to the bodyside liner 142 and/or the outercover 140 utilizing the methods described above. The liner 142 can be coextensive with the outercover 140 or can be larger or smaller than the outercover 140.

As discussed herein, the discrete absorbent composite 90 includes a first sheet 92 and a second sheet 93 joined together at a plurality of bond points 45. The absorbent core 91 is located between the first and second sheets 92 and 93 and the bond points 45 extend through the holes 41 within the absorbent core 91.

The diaper 120 can optionally include a pair of containment flaps 155 for inhibiting the lateral flow of body exudates. The containment flaps 155 can be operatively attached to the diaper 120 in any suitable manner as is well known in the art. In particular, suitable constructions and arrangements for the containment flaps are generally well known to those skilled in the art and are described in U.S. Pat. No. 4,704,116 issued Nov. 3, 1987, to Enloe, which is incorporated herein by reference to the extent that it is consistent (i.e., not in conflict) herewith.

To further enhance containment and/or absorption of body exudates, the diaper 120 may optionally include waist elastic members 154 in the front and/or back waist regions 122 and 124 of the diaper 120. Likewise, the diaper 120 may optionally include leg elastic members 158, as are known to those skilled in the art. The waist elastic members 154 and the leg elastic members 158 can be formed of any suitable elastic material that is well known to those skilled in the art. For example, suitable elastic materials include sheets, strands or ribbons of natural rubber, synthetic rubber, or thermoplastic elastomeric polymers. In one aspect of the invention, the waist elastics and/or the leg elastics may include a plurality of dry-spun coalesced multi-filament spandex elastomeric threads sold under the trade name LYCRA and available from Invista of Wilmington, Del., U.S.A.

The outercover 140 may suitably include a material that is substantially liquid impermeable. The outercover 140 may be provided by a single layer of liquid impermeable material, or more suitably include a multi-layered laminate structure in which at least one of the layers is liquid impermeable. In particular aspects, the outer layer may suitably provide a relatively cloth-like texture to the wearer. A suitable liquid impermeable film for use as a liquid impermeable inner layer, or a single layer liquid impermeable outercover 140 is a 0.025 millimeter (1.0 mil) polyethylene film commercially available from Edison Plastics Company of South Plainfield, N.J., U.S.A. Alternatively, the outercover 140 may include a woven or nonwoven fibrous web layer that has been totally or partially constructed or treated to impart the desired levels of liquid impermeability to selected regions that are adjacent or proximate the absorbent body.

The outercover 140 may also be stretchable, and in some aspects it may be elastomeric. For example, such an outercover material can include a 0.3 osy polypropylene spunbond that is necked 60 percent in the lateral direction, creped 60 percent in the longitudinal direction, and laminated with 3 grams per square meter (gsm) Bostik-Findley H2525A styrene-isoprene-styrene based adhesive to 8 gsm PEBAX 2533 film with 20 percent $TiO_2$ concentrate. Reference is made to U.S. Pat. No. 5,883,028, issued to Morman et al., U.S. Pat. No. 5,116,662 issued to Morman and U.S. Pat. No. 5,114,781 issued to Morman, all of which are hereby incorporated herein by reference, for additional information regarding suitable outercover materials.

The bodyside liner 142 is suitably compliant, soft-feeling, and non-irritating to the wearer's skin. The bodyside liner 142 is also sufficiently liquid permeable to permit liquid body exudates to readily penetrate through its thickness to the absorbent composite 90 and the absorbent core 91 located therein. A suitable liquid permeable bodyside liner 142 is a nonwoven polyethylene/polypropylene bi-component web having a basis weight of about 27 gsm; the web may be spunbonded or a bonded carded web. Optionally, the bodyside liner 142 may be treated with a surfactant to increase the wettability of the liner material.

Alternatively, the bodyside liner 142 may also be stretchable, and in some aspects it may be elastomeric. For instance, the liner 142 can be a nonwoven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) can be adhered to the necked spunbond material to impart elasticity to the spunbond fabric. The fabric can be surface treated with an operative amount of surfactant, such as about 0.6 percent AHCOVEL Base N62 surfactant, available from ICI Americas, a business having offices in Wilmington, Del., U.S.A. Other suitable materials may be extensible biaxially stretchable materials, such as a neck stretched/creped spunbond. Reference is made to U.S. Pat. No. 6,552,245, issued Apr. 22, 2003, to Roessler et al., which is incorporated by reference herein to the extent that it is consistent (i.e., not in conflict) herewith.

The absorbent core 91 includes absorbent material 26 and is suitably compressible, conformable, and capable of absorbing and retaining liquid body exudates released by the wearer. For example, the absorbent core 91 can include a matrix of absorbent fibers, and more suitably cellulosic fluff, such as wood pulp fluff, and superabsorbent particles. One suitable pulp fluff is identified with the trade designation CR1654, commercially available from U.S. Alliance, Childersburg, Ala., U.S.A. As an alternative to wood pulp fluff, synthetic fibers, polymeric fibers, meltblown fibers, short cut homofil bicomponent synthetic fibers, or other natural fibers may be used. Suitable superabsorbent materials can be selected from natural, synthetic, and modified natural polymers and materials. The superabsorbent materials can be inorganic materials, such as silica gels, or organic compounds, such as cross linked polymers, for example, sodium neutralized polyacrylic acid. Suitable superabsorbent materials are available from various commercial vendors, such as Dow Chemical Company of Midland, Mich., U.S.A., and Stockhausen Inc., Greensboro, N.C., U.S.A.

In various embodiments, the absorbent core 91 may include 30 to 90 percent superabsorbent by weight. In some embodiments, the absorbent core 91 may include at least 50, at least 60, at least 70, or at least 80 percent superabsorbent by weight. In various embodiments, the absorbent core 91 may include 70 to 10 percent cellulose fluff by weight. In some embodiments, the absorbent core 91 may include less than 70, less than 60, less than 50, less than 40, less than 30, or less than 20 percent cellulose fluff by weight. In some embodiments, the absorbent core 91 may include 50 to 90 percent superabsorbent material by weight and 50 to 10 percent cellulose fluff by weight. In some embodiments, the absorbent core 91 may include 60 to 90 percent superabsorbent material by weight and 40 to 10 percent cellulose fluff by weight. In some embodiments, the absorbent core 91 may include 70 to 90 percent superabsorbent material by weight and 30 to 10 percent cellulose fluff by weight.

The absorbent core 91 and/or the absorbent composite 90 may have a variety of shapes and configurations as are known in the art, such as rectangular, hourglass shaped, I-shaped, and the like. The absorbent core 91 may have the same shape or a different shape than the absorbent composite 90. For example, the absorbent core 91 may have a rectangular shape and the absorbent composite 90 may have a rectangular shape. In another example, the absorbent core 91 may have an hourglass shape and the absorbent composite 90 may have a rectangular shape.

In some embodiments, the portions of the absorbent composite 90 including the absorbent core 91 may have a density within the range of about 0.10 to about 0.5 grams per cubic centimeter. The absorbent core 91 of the present invention may have a uniform density. In other words, the portions of the absorbent core 91 proximate the holes 41 may have essentially the same density as the portions of the absorbent core 91 more distant from the holes 41. This uniform density is believed to provide for a soft and conforming absorbent composite 90 without hard spots or hard lines in the product.

Traditional cellulose fluff based absorbent products have been made thinner by greater compression resulting in higher densities and less flexibility. Alternatively, thinner absorbent products have been made with less absorbent material but may not have the absorbent capacity necessary to meet the needs of the wearer. However, as higher concentrations of superabsorbent materials have become more prevalent, thinner absorbent articles with adequate absorbent capacity have been manufactured. Unfortunately, absorbent articles with high concentrations of superabsorbent material have also traditionally suffered from structural breakdowns, superabsorbent shifting, and superabsorbent migration because the relative percentage of cellulose fluff "holding" the superabsorbent in place has decreased relative to the superabsorbent material contained therein.

In general, the method and apparatus of the present invention is compatible with relatively thin absorbent cores 91. For example, in various embodiments, the absorbent core 91 and/or absorbent composite 90 can have a thickness of about 1 mm to about 10 mm. In some embodiments, the absorbent core 91 and/or the absorbent composite 90 may have a thickness of less than about 9 mm, less than about 8 mm, less than about 7 mm, less than about 6 mm, less than about 5 mm, less than about 4 mm, less than about 3 mm, or less than about 2 mm. The thin absorbent core 91 of the present invention allows for a thinner absorbent article. Thin absorbent articles are generally believed to be well suited for comfort and discretion. As used herein, the thickness of the absorbent composite 90 describes the thickness as measured in those portions including the absorbent core 91. One skilled in the art will appreciate that portions of the absorbent composite 90 may not include the absorbent core 91 (for example, the marginal areas 42) and would obviously be thinner at these locations.

Figure 10:
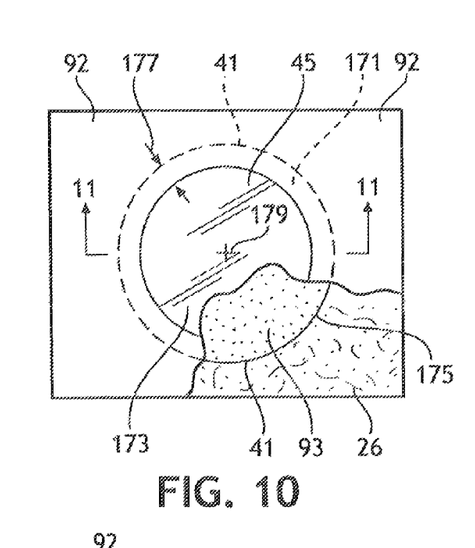
FIG. 10 representatively illustrates the portion of the absorbent composite of FIG. 9 delineated by box 10.
Figure 11:
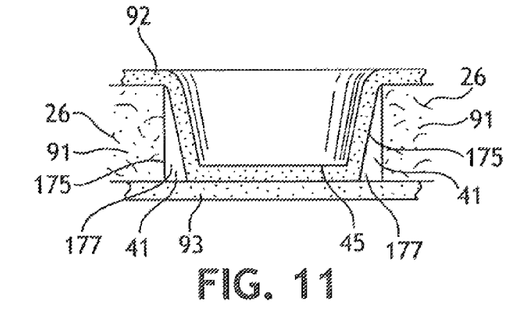
FIG. 11 representatively illustrates a cross sectional view of FIG. 10 taken along the line 11-11.

The present invention includes a thin absorbent composite having a stabilized absorbent core wherein structural breakdowns, superabsorbent shifting, and superabsorbent migration are believed to be limited. The stabilized absorbent composites include a first sheet joined to a second sheet at a plurality of bond points corresponding with a plurality of holes located within an absorbent core. FIG. 9 representatively illustrates an exemplary absorbent composite 90. Portions of the absorbent composite 90 are cut away in FIG. 9 to illustrated underlying features. FIG. 10 representatively illustrates the portion of FIG. 9 delineated by box 10 and magnified for clarity and with portions cut away to illustrate underlying details. FIG. 11 is a cross sectional view of the portion of the absorbent composite 90 illustrated in FIG. 10.

Referring now to FIGS. 9, 10 and 11, the absorbent composite 90 includes a first sheet 92, a second sheet 93, and a discrete unitary absorbent core 91 located therebetween. The absorbent core 91 has a plurality of holes 41 extending there through and is positioned between the first sheet 92 and the second sheet 93. The first sheet 92 extends through the holes 41 in the absorbent core 91 and is joined with the second sheet 93 at a plurality of bond points 45. The plurality of bond points 45 stabilize the absorbent core 91 and the absorbent composite 90. Therefore, the resulting absorbent composite 90 includes a stabilized discrete unitary absorbent core 91 that is believed to be thin, soft, and compliant having no ridges, hard lines, or hard spots.

The unitary absorbent cores of the present invention have overall "continuity" (i.e., no segmenting) and are believed to promote free fluid movement throughout the entire core. The bond points are believed to improve the integrity of the absorbent composite, but the relatively small holes maintain a large absorbent area available to receive insults. Additionally, it is believed that the unitary absorbent cores with uniform densities will bend continuously and evenly about the wearer. Finally, it is believed that unitary absorbent cores will distribute the weight of the wearer more evenly and won't result in pressure points possible with discontinuous absorbent cores.

The holes 41 in the absorbent core 91 may have any suitable shape and any suitable size. For example, the holes 41 may have a circular shape, as illustrated in FIG. 9, but may alternatively be in the shape of an oval, square, triangle, or any other suitable geometric shape, irregular, or the like, or combinations thereof. In some embodiments, the absorbent cores 91 may have at least one first hole having a first shape and at least one second hole having a second shape wherein the first shape and the second shape are different. In some embodiments, the absorbent cores 91 may have at least one first hole having a first size and at least one second hole having a second size wherein the first size and the second size are different.

In various embodiments, the holes 41 may have a hole area 171 of 1 mm$^2$ (0.0015 in$^2$) to 200 mm$^2$ (0.3 in$^2$), 1 mm$^2$ (0.0015 in$^2$) to 100 mm$^2$ (0.155 in$^2$), or 1 mm$^2$ (0.0015 in$^2$) to 25 mm$^2$ (0.03875 in$^2$). In some embodiments, the hole area 171 may be less than 200 mm$^2$, less than 100 mm$^2$, less than 90 mm$^2$, less than 80 mm$^2$, less than 70 mm$^2$, less than 60 mm$^2$, less than 50 mm$^2$, less than 40 mm$^2$, less than 30 mm$^2$, less than 20 mm$^2$, or less than 10 mm$^2$. In embodiments wherein the holes 41 have a generally circular shape, the holes 41 may have a diameter of 1 mm to 16 mm, 1 mm to 10 mm, or 1 mm to 5 mm. In some embodiments the holes 41 may have a diameter of less than 16 mm, less than 10 mm, or less than 5 mm. In various embodiments, the total area of the holes 41 may be between about 1 to about 33 percent, about 1 to about 25 percent, or less than about 10 percent of the total area of the absorbent core 91.

In various embodiments, the absorbent cores may have at least one first hole having a first hole area and at least one second hole having a second hole area wherein the first and second hole areas are different. For example, in some embodiments, the absorbent cores may define a front portion generally oriented towards the front waist region of the absorbent article and a back portion generally oriented towards the back waist region of the absorbent article wherein the back portion includes holes having a larger hole area and wherein the front portion includes holes having a smaller hole area.

The absorbent material surrounding the holes 41 defines a hole wall 175. The hole wall 175 is preferably no more or less dense than any other portion of the absorbent core 91 which is believed to be more comfortable to the wearer. In contrast, some traditional methods of stabilizing absorbent cores, such as pin aperturing, embossing, needling, and the like, have resulted in densified regions surrounding indentations. Such densifications may impact fluid movement within the absorbent core, may be noticeable to a wearer and/or caregiver, and may reduce the flexibility of the absorbent core 91.

The bonds 45 may be any suitable shape and any suitable size. For example, the bonds 45 may be circular, as illustrated in FIG. 10, but may also be oval, square, triangular, or any other suitable geometric shape, irregular, or the like, or combinations thereof. In some embodiments, the absorbent cores 91 may have at least one first bond having a first shape and at least one second bond having a second shape wherein the first shape and the second shape are different. In some embodiments, the absorbent cores 91 may have at least one first bond having a first size and at least one second bond having a second size wherein the first size and the second size are different.

In some embodiments, the bonds 45 may have a bond area 173 of 1 mm$^2$ (0.0015 in$^2$) to 200 mm$^2$ (0.3 in$^2$), 1 mm$^2$ (0.0015 in$^2$) to 100 mm$^2$ (0.155 in$^2$), or 1 mm$^2$ (0.0015 in$^2$) to 25 mm$^2$ (0.03875 in$^2$). In some embodiments, the bond area 173 may be less than 200 mm$^2$, less than 100 mm$^2$, less than 90 mm$^2$, less than 80 mm$^2$, less than 70 mm$^2$, less than 60 mm$^2$, less than 50 mm$^2$, less than 40 mm$^2$, less than 30 mm$^2$, less than 20 mm², or less than 10 mm². In embodiments wherein the bonds 45 generally have a circular shape, the bonds 45 may have a diameter of 1 mm to 16 mm, 1 mm to 10 mm, or 1 mm to 5 mm. In some embodiments the bonds 45 may have a diameter of less than 16 mm, less than 10 mm, or less than 5 mm.

In various embodiments, the absorbent cores 91 may have at least one first bond having a first bond area and at least one second bond having a second bond area wherein the first and second bond areas are different. For example, in some embodiments, the absorbent cores may define a front portion generally oriented towards the front waist region of the absorbent article and a back portion generally oriented towards the back waist region of the absorbent article wherein the back portion includes bonds having a larger bond area and wherein the front portion includes bonds having a smaller bond area.

In some embodiments, larger bonds and smaller bonds may be intermixed throughout the absorbent core in any suitable arrangement. In some embodiments, smaller bonds may be adapted to release when the absorbent material is wetted. In some embodiments, larger bonds may be adapted to remain joined when the absorbent material is wetted.

In some embodiments, the bond area 173 is at least 60, 70, 80, 90, or 95 percent that of the hole area 171, resulting in an unbonded area 177 that is less than 40, 30, 20, 10, or 5 percent of the hole area 171. It is believed that having the bond area 173 close to the same size as the hole area 171 results in greater stabilization of the absorbent core 91 because less of the absorbent material 26 is unsupported, i.e., there is less unbonded area 177. For example, as illustrated in FIG. 10, the bond area 173 is approximately 60 percent of the hole area 171, whereas the unbonded area 177 is about 40 percent of the hole area 171.

In some embodiments, the bond area 173 may be substantially devoid of absorbent material 26. In other words, the first sheet 92 may be joined directly to the second sheet 93 at the bond points 45 with substantially no absorbent material 26 therebetween. In some embodiments, the bond area 173 may be free of absorbent material 26. In other words, the first sheet 92 may be joined directly to the second sheet 93 at the bond points 45 with no absorbent material 26 therebetween as illustrated in FIG. 11.

As illustrated in FIG. 11, the bonds 45 are skewed towards the second sheet 93. As such, the first sheet 92 extends at least partially through the holes 41 of the absorbent core 91. In some embodiments, the first sheet 92 extends entirely through the holes 41 of the absorbent core 91. In one embodiment, the first sheet 92 may be positioned towards the liner 142 and the second sheet 93 may be oriented towards the outercover 140. In another embodiment, the second sheet 93 may be positioned towards the liner 142 and the first sheet 92 may be oriented towards the outercover 140.

In various embodiments, the bonds 45 may be generally located within the holes 41. In some embodiments, the bonds 45 may be registered within the holes 41. In other words, the bonds 45 may be generally centered within the holes 41. For a bond 45 to be generally centered within the hole 41 means that the bonds 45 have a center point and the holes 41 have a center point and both center points coincide at common center point 179 as illustrated in FIG. 10. In some embodiments, at least 60, at least 70, at least 80, at least 90, and at least 99 percent of the bonds 45 are located with the holes 41. In some embodiments, 100 percent of the bonds 45 are located within the holes 41. In some embodiments, at least 60, at least 70, at least 80, at least 90, and at least 99 percent of the bonds 45 are registered within the holes 41. In some embodiments, 100 percent of the bonds 45 are registered within the holes 41.

In various embodiments, the absorbent composite may have a "bond point density" of 0.05 to 1.0 bond points 45 per square centimeter of absorbent core 91. In some embodiments, the absorbent composite may have 0.1 to 0.5 bond points 45 per square centimeter of absorbent core 91. In some embodiments, the absorbent composite may have 0.2 to 0.4 bond points 45 per square centimeter of absorbent core 91. In some embodiments, the absorbent core 91 may have a first bond point density in a first region and a second bond point density in a second region. For example, the absorbent core 91 may have a front portion located generally towards the front waist region of the absorbent article and a back portion located generally towards the back waist region of the absorbent article wherein the front portion has a higher density of bond points and the back portion has a lower density of bond points. In some embodiments, the bond points 45 may have a diameter, D, and may be spaced apart by at least one times, two times, three times, or more than four times the diameter, D.

In various embodiments, the absorbent composite 90 may include an absorbent core 91 located between a liquid pervious first sheet 92 and a liquid pervious second sheet 93. The liquid pervious first sheet 92 extends through holes 41 in the absorbent core 91 to join with the liquid pervious second sheet 93 at a plurality of bond points 45. In various embodiments, the absorbent composite 90 may include an absorbent core 91 located between a liquid impervious first sheet 92 and a liquid pervious second sheet 93. The liquid impervious first sheet 92 extends through holes 41 in the absorbent core 91 to join with the liquid pervious second sheet 93 at a plurality of bond points 45. In various embodiments, the absorbent composite 90 may include an absorbent core 91 located between a liquid pervious first sheet 92 and a liquid impervious second sheet 93. The liquid pervious first sheet 92, extends through holes 41 in the absorbent core 91 to join with the liquid impervious second sheet 93 at a plurality of bond points 45. In various embodiments, the first sheet 92 or the second sheet 93 may face towards the liner 142.

In one aspect, the absorbent composite 90 may be stretchable so as not to inhibit the stretchability of other components to which the absorbent composite 90 may be adhered, such as the outercover 140 and/or the bodyside liner 142. For example, the absorbent composite 90 may include materials disclosed in U.S. Pat. Nos. 5,964,743, 5,645,542, 6,231,557, 6,362,389, and international patent application WO 03/051254, the disclosure of each of which is incorporated by reference herein to the extent that they are consistent (i.e., not in conflict) herewith.

In some aspects, a surge management layer (not shown) may be included in the diaper 120. The surge management layer may be positioned in the diaper 120 in a variety of locations as is known in the art. For example, the surge management layer can be proximate the absorbent composite 90, for example between the absorbent composite 90 and the bodyside liner 142, and attached to one or more components of the diaper 120 by methods known in the art, such as by adhesive, ultrasonic bonding, pressure bonding, thermal bonding, and the like, or combinations thereof.

A surge management layer helps to decelerate and diffuse surges or gushes of liquid that may be rapidly introduced into the absorbent composite 90. Desirably, the surge management layer can rapidly accept and temporarily hold the liquid prior to releasing the liquid into the storage or retention portions of the absorbent composite 90. Examples of suitable surge management layers are described in U.S. Pat. No. 5,486,166 and U.S. Pat. No. 5,490,846, the contents of which are incorporated herein by reference to the extent that they are consistent (i.e., not in conflict) herewith.

While the invention has been described in detail with respect to specific embodiments thereof, it will be appreciated that those skilled in the art, upon attaining understanding of the foregoing will readily appreciate alterations to, variations of, and equivalents to these embodiments. Accordingly, the scope of the present invention should be assessed as that of the appended claims and any equivalents thereto.

The invention claimed is:

1. An absorbent article comprising:
   a. a liquid pervious liner;
   b. a liquid impervious backsheet; and
   c. an absorbent composite located between the liner and the back sheet, the absorbent composite comprising,
      i. a first sheet;
      ii. a second sheet;
      iii. 50 to 90 percent superabsorbent particles; and
      iv. a unitary absorbent core having a plurality of holes there through; the unitary absorbent core having a uniform density and being positioned between the first sheet and the second sheet, the first sheet being joined with the second sheet at a plurality of bond points, the bond points being located within the holes and being substantially devoid of absorbent material wherein the bond points have a diameter and are separated by at least four times the diameter.

2. The absorbent article of claim 1 wherein the absorbent composite has a thickness of less than 6 mm.

3. The absorbent article of claim 1 wherein at least 90 percent of the holes have a bond point registered therein.

4. The absorbent article of claim 1 wherein the absorbent core defines a total absorbent core area and the holes areas define a total hole area that is less than 25 percent of the total absorbent core area.

5. The absorbent article of claim 1 wherein each bond point defines a bond area that is at least 60 percent of the hole area.

6. The absorbent article of claim 1 wherein each hole has a hole area less than 200 mm.

7. The absorbent article of claim 1 wherein the bond points are skewed towards the second sheet.

8. The absorbent article of claim 7 wherein the first sheet may face towards the liner.

9. The absorbent article of claim 7 wherein the second sheet may face towards the liner.

10. An absorbent article comprising:
    a. a liquid pervious liner;
    b. a liquid impervious backsheet; and
    c. an absorbent composite located between the liner and the backsheet, the absorbent composite comprising,
       i. a first sheet;
       ii. a second sheet;
       iii. 50 to 90 percent superabsorbent particles; and
       iv. a unitary absorbent core having a plurality of holes there through, each hole having a hole area less than 200 mm$^2$; the unitary absorbent core being positioned between the first sheet and the second sheet, the first sheet being joined with the second sheet at a plurality of bond points, the bond points being located within the holes and being substantially devoid of absorbent material wherein the bond points have a diameter and are separated by at least four times the diameter.

11. The absorbent article of claim 10 wherein the absorbent composite has a thickness of less than 6 mm.

12. The absorbent article of claim 10 wherein at least 90 percent of the holes have a bond point registered therein.

13. The absorbent article of claim 10 wherein the absorbent core defines a total absorbent core area and the holes areas define a total hole area that is less than 25 percent of the total absorbent core area.

14. The absorbent article of claim 10 wherein each bond point defines a bond area that is at least 60 percent of the hole area.

15. The absorbent article of claim 10 wherein the unitary absorbent core has a uniform density.

16. The absorbent article of claim 10 wherein the bond points are skewed towards the second sheet.

17. The absorbent article of claim 16 wherein the first sheet may face towards the liner.

18. The absorbent article of claim 16 wherein the second sheet may face towards the liner.

19. An absorbent article comprising:
    a. a liquid pervious liner;
    b. a liquid impervious backsheet; and
    c. an absorbent composite located between the liner and the backsheet, the absorbent composite comprising,
       i. a first sheet comprising a forming section and a wrap section;
       ii. 50 to 90 percent superabsorbent particles; and
       iii. a unitary absorbent core having a plurality of holes there through; the unitary absorbent core being positioned between the forming section and the wrap section of the first sheet, the forming section being joined with the wrap section of the first sheet at a plurality of bond points, the bond points being located within the holes and being substantially devoid of absorbent material wherein the bond points have a diameter and are separated by at least four times the diameter.

20. The absorbent article of claim 19 wherein the absorbent composite has a thickness of less than 6 mm.

21. The absorbent article of claim 19 wherein at least 90 percent of the holes have a bond point registered therein.

22. The absorbent article of claim 19 wherein the absorbent core defines a total absorbent core area and the holes areas define a total hole area that is less than 25 percent of the total absorbent core area.

23. The absorbent article of claim 19 wherein each bond point defines a bond area that is at least 60 percent of the hole area.

24. The absorbent article of claim 19 wherein each hole has a hole area less than 200 mm.

25. The absorbent article of claim 19 wherein the unitary absorbent core has a uniform density.

* * * * *